US007393547B2

(12) United States Patent
Nelson

(10) Patent No.: US 7,393,547 B2
(45) Date of Patent: Jul. 1, 2008

(54) ANTIMICROBIAL ELASTOMER COMPOSITION AND METHOD FOR MAKING

(75) Inventor: Jesse N. Nelson, Oxnard, CA (US)

(73) Assignee: Helix Medical, LLC, Plymouth, MI (US)

( * ) Notice: Subject to any disclaimer, the term of this patent is extended or adjusted under 35 U.S.C. 154(b) by 0 days.

(21) Appl. No.: 10/923,138

(22) Filed: Aug. 19, 2004

(65) Prior Publication Data

US 2005/0020844 A1 Jan. 27, 2005

Related U.S. Application Data

(63) Continuation-in-part of application No. 09/833,961, filed on Apr. 11, 2001, now abandoned.

(51) Int. Cl.
*A61K 33/38* (2006.01)
*A61K 9/14* (2006.01)
*A01N 59/16* (2006.01)

(52) U.S. Cl. .................................. 424/618; 424/486
(58) Field of Classification Search ........................ None
See application file for complete search history.

(56) References Cited

U.S. PATENT DOCUMENTS

| | | | | |
|---|---|---|---|---|
| 3,445,420 | A | * | 5/1969 | Kookootsedes et al. ..... 524/862 |
| 3,932,627 | A | | 1/1976 | Margraf |
| 3,932,629 | A | | 1/1976 | Dawes et al. |
| 4,054,139 | A | | 10/1977 | Crossley |
| 4,435,853 | A | | 3/1984 | Blom et al. |
| 4,483,688 | A | | 11/1984 | Akiyama |
| 4,563,485 | A | | 1/1986 | Fox, Jr. et al. |
| 4,581,028 | A | | 4/1986 | Fox, Jr. et al. |
| 4,592,920 | A | | 6/1986 | Murtfeldt |
| 4,603,152 | A | | 7/1986 | Laurin et al. |
| 4,612,337 | A | | 9/1986 | Fox, Jr. et al. |
| 4,615,705 | A | | 10/1986 | Scales et al. |
| 4,677,143 | A | | 6/1987 | Laurin et al. |
| 5,019,096 | A | | 5/1991 | Fox, Jr. et al. |
| 5,314,470 | A | | 5/1994 | Persson |
| 5,474,797 | A | | 12/1995 | Sioshansi et al. |
| 5,480,432 | A | | 1/1996 | Suding et al. |
| 5,507,809 | A | | 4/1996 | Blom |
| 5,520,664 | A | | 5/1996 | Bricault, Jr. et al. |
| 5,567,495 | A | | 10/1996 | Modak et al. |
| 5,578,083 | A | | 11/1996 | Laguette et al. |
| 5,624,704 | A | | 4/1997 | Darouiche et al. |
| 5,772,640 | A | | 6/1998 | Modak et al. |
| 5,902,283 | A | | 5/1999 | Darouiche et al. |
| 5,928,569 | A | | 7/1999 | Reo |
| 5,928,570 | A | * | 7/1999 | Reo ........................... 252/514 |
| 5,957,978 | A | | 9/1999 | Blom |
| 6,013,711 | A | * | 1/2000 | Lewis et al. ................ 524/265 |
| 6,017,587 | A | | 1/2000 | Kleyer et al. |
| 6,083,208 | A | | 7/2000 | Modak et al. |
| 6,106,505 | A | | 8/2000 | Modak et al. |
| 6,361,526 | B1 | * | 3/2002 | Reisdorf et al. ............. 604/265 |
| 6,887,270 | B2 | | 5/2005 | Miller et al. |
| 6,948,526 | B2 | | 9/2005 | Seder et al. |
| 7,081,133 | B2 | | 7/2006 | Chinn et al. |
| 2002/0022136 | A1 | | 2/2002 | Valade et al. |
| 2002/0193879 | A1 | | 12/2002 | Seder et al. |
| 2005/0049350 | A1 | | 3/2005 | Tonapi et al. |
| 2005/0148721 | A1 | | 7/2005 | Tonapi et al. |
| 2005/0161859 | A1 | | 7/2005 | Miller et al. |
| 2005/0239940 | A1 | | 10/2005 | Shima et al. |
| 2005/0256573 | A1 | | 11/2005 | Seder et al. |
| 2006/0047043 | A1 | | 3/2006 | Nakayoski et al. |

FOREIGN PATENT DOCUMENTS

| | | |
|---|---|---|
| EP | 0222509 A2 | 10/1986 |
| WO | WO 97/14447 | 4/1997 |
| WO | WO 97/45075 | 12/1997 |
| WO | WO 98/04463 | 2/1998 |
| WO | WO 98/08463 | 3/1998 |
| WO | WO 03/057083 | 7/2003 |
| WO | WO 03/082983 | 10/2003 |
| WO | WO 2004/050753 | 6/2004 |
| WO | WO 2004/046233 | 7/2004 |
| WO | WO 2005/014074 | 2/2005 |
| WO | WO 2005/087135 | 9/2005 |

OTHER PUBLICATIONS

International Search Report (Nov. 29, 2005), International Preliminary Report on Patentability (Feb. 20, 2007), and Written Opinion of the International Searching Authority (Feb. 19, 2007) for PCT/US2005/26723 (15 pages).

International Search Report (Apr. 4, 2003) and International Preliminary Report on Patentability (Jun. 25, 2004) for PCT/US2002/11653 (7 pages).

Everaert et al., "Biofilm Formation In Vivo on PerfluoroAlkylsiloxane-Modified Voice Prostheses" Arch Otolaryngol Head Neck Surg. vol. 125, Dec. 1999. pp. 1329-1332.

* cited by examiner

*Primary Examiner*—Johann Richter
*Assistant Examiner*—Ernst V Arnold
(74) *Attorney, Agent, or Firm*—Ronald W. Wangerow; Harness, Dickey & Pierce, P.L.C.

(57) ABSTRACT

A method for making an elastomeric material containing an antimicrobial composition such as a dispersion of silver oxide that is suitable for implantation within the body. The elastomer made in accordance with this method extends the amount of work-time available for processing the elastomer into an article as compared with the work-time available when using prior art compounding methods.

16 Claims, No Drawings

ANTIMICROBIAL ELASTOMER COMPOSITION AND METHOD FOR MAKING

BACKGROUND OF THE INVENTION

1. Field of the Invention

The present invention relates to a method for making an antimicrobial elastomeric material containing an antimicrobial composition such as a dispersion of silver oxide that is suitable for implantation within the body

2. Prior Art

Medical devices, particularly implantable elastomeric prostheses which are used in environments where microorganisms are actively growing, can become covered with a biofilm comprising a colonized layer of microorganisms such that the function of the prosthesis is impaired. After growth of the biofilm microbial layer, filaments can grow and descend into the body or wall of the prosthesis and detrimentally affect its physical properties until the device no longer functions. The fouled device must be cleaned or discarded.

Whenever a prosthesis is in contact with moisture in a warm, nutrient rich environment, the surfaces of the prosthesis may support microbial growth which may include, inter alia, bacteria. The microbial growth can interfere with the functioning of the prosthesis, requiring removal of the prosthesis for disposal or cleaning. The microbial growth is a persistent problem in the management and care of patients who have had their larynx removed and utilize a voice prosthesis since the prosthesis is exposed to a non-sterile, humid, warm, nutrient rich environment.

Various methods for preventing microbial growth on an indwelling device have been proposed. One approach for reducing bacterial infection encountered with the use of medical devices inserted into body cavities has been to apply an antimicrobial coating to the surface of the medical device. For example, U.S. Pat. No. 4,592,920 to Murtfeldt; U.S. Pat. No. 4,603,152 to Laurin et al and U.S. Pat. No. 4,677,143 to Laurin et al. each teach applying a coating containing an antimicrobial agent such as silver oxide to the outer surfaces of medical devices such as catheters, enteral feeding tubes, endotracheal tubes and other hollow tubular devices. The '920 patent to Murtfeldt is primarily concerned with providing a surface coating of an antimicrobial metal compound on a medical device such as a catheter, but also discloses that the metal compound can be "imbedded" within the entire catheter. However, the Murtfeldt patent teaches that the imbedded construction is less desirable since the antimicrobial metal compound imbedded within the side wall of the catheter has less likelihood of encountering migrating microbes and, by inference, is less effective than a surface coating.

Seder et al., in pending U.S. patent application Ser. No. 09/833,961, the content of which is incorporated herein by reference thereto, teach that antimicrobial agents can be compounded (i.e., embedded) into those portions of a prosthesis that are not in contact with tissue. The antimicrobial portions remain free of microbial growth for an extended period which contributes to longer use of the prosthesis in vivo. For example, the valve in most voice prostheses is not in contact with tissue. It is only in intermittent contact with body fluids. The same is true of the inside surface of the tubular prosthesis and/or the facial and inside surfaces of rings or cartridges that are present to reinforce the soft body of a prosthesis. By adding an amount of microbial agent effective to resist growth onto (or into) the valve, ring or cartridge, it is found that microbial growth is delayed for a significant period without any evidence of irritation or toxicity to the tissue. Seder et al. further teach that the antimicrobial agent-bearing elastomer can be compounded by dispersion of the antimicrobial agent into the raw elastomer material. For example, silicone elastomer can contain at least 10 percent of an antimicrobial agent such as silver, or silver compounds such as silver oxide. Other suitable antimicrobial compounds such as, for example, gold, platinum, copper, zinc metal powder or oxides and salts thereof, can be used in the non-tissue contacting portions of the prosthesis. A more complete discussion of prior art methods for incorporating antimicrobial agents into, or upon, a prosthesis is also presented in Seder et al.

A problem with prior art methods of dispersing an antimicrobial agent such as $Ag_2O$ into an elastomer prior to forming a prosthetic article therefrom is the short work-time available for forming the elastomer into a prosthesis, or a portion thereof, after compounding; sometimes the work-time being as short as a minute or two. It is, therefore, desirable to provide a method for incorporating an antimicrobial agent such as, for example, silver oxide, into an elastomer such as silicone that provides a longer work-time for fabricating an article therefrom.

SUMMARY

The present invention is directed to an antimicrobial elastomer composition and a method for making the composition that substantially obviates one or more of the limitations of the related art. To achieve these and other advantages and in accordance with the purpose of the invention, as embodied and broadly described herein, the method of making the antimicrobial elastomer of the present invention includes the steps of: (a) presenting a two-part, addition-curable silicone elastomeric dispersion consisting of Part A and Part B; (b) mixing part A with part B to form a liquid, moldable silicone elastomer; (c) dispersing additional inhibitor into the silicone elastomer wherein the inhibitor is any agent that affects the cure time of the liquid elastomer; and (d) compounding an antimicrobial agent into the liquid silicone elastomer. The resulting liquid silicone may be molded to form an article over an extended period of time (i.e., "work-time"). In a second embodiment of the method of the present invention, the mixing of Part A and Part B may be delayed by adding additional inhibitor to one or both parts of the silicone, followed by the addition of the antimicrobial agent to one or both parts of the silicone prior to the step of mixing Part A and Part B.

The features of the invention believed to be novel are set forth with particularity in the appended claims. However the invention itself, both as to organization and method of operation, together with further objects and advantages thereof may be best understood by reference to the following description.

DESCRIPTION OF THE PREFERRED EMBODIMENTS

A first preferred method for making an antimicrobial elastomeric composition in accordance with the present invention comprises the steps of: (a) presenting Part A and Part B of a silicone elastomer wherein when Part A and Part B are mixed together in the presence of an initiator, a curable, injection moldable silicone elastomer is formed; (b) mixing part A with part B to form a liquid, moldable silicone elastomer; (c) dispersing additional inhibitor into the silicone elastomer wherein the inhibitor is any agent that affects the cure time of the liquid elastomer; and (d) compounding an antimicrobial agent into the liquid silicone elastomer.

A second preferrend method for making an antimicrobial elastomeric composition in accordance with the present invention comprises the steps of: (a) presenting Part A and Part B of a silicone elastomer wherein when Part A and Part B are mixed together in the presence of an initiator, a curable, injection moldable silicone elastomer is formed; (b) adding additional inhibitor to Part A or Part B; (c) dispersing particles of an antimicrobial agent in Part A or Part B; and (d) mixing Part A with Part B.

In yet a third preferred method for making an antimicrobial elastomeric composition in accordance with the present invention, the method comprises the steps of (a) presenting Part A and Part B of a silicone elastomer; again wherein when Part A and Part B are mixed together in the presence of an initiator, a curable, injection moldable silicone elastomer is formed; (b) adding additional inhibitor to both Part A and Part B; (c) dispersing particles of an antimicrobial agent in Part A or Part B; and (d) mixing Part A with Part B.

In all of the methods for making an antimicrobial silicone elastomer having an extended work-time in accordance with the present invention, the preferred antimicrobial agent is silver oxide. It is clear to artisans that in order to form an elastomeric article by injection molding, the moldable elastomer comprising the article must be in a physical form operable for conforming to the contour of a mold into which it is injected. The term "work-time", as used herein, means the length of time after Part A and Part B of a 2-part elastomer composition are admixed that the elastomer composition remains injection moldable at or near room temperature. Part A and Part B are preferably platinum cured and provide a silicone elastomer having a durometer between 40 and 70, and most preferably about 60, when cured. Although the amount of inhibitor incorporated into Part B of a 2-part silicone elastomer by the manufacturer is generally maintained as a trade secret by the manufacturer, it is believed to be on the order of 0.02% w/w as supplied. The term "inhibitor", as used herein, refers to any substance that, when added to a silicone elastomer comprising a mixture of Part A and Part B, increases or extends the work-time (i.e., the time required for the elastomer to cure). An example of a suitable inhibitor is 2-methyl-3-butyn-2-ol. The amount of additional inhibitor to be added to Part A and/or Part B, either prior to or after mixing, is related to the amount of work-time altering additive such as silver oxide added to the elastomer. The amount of additional inhibitor added to the silicone elastomer in accordance with the method of the present invention is in the range of 0.05-0.40% w/w, and preferably in the range 0.05-0.1% w/w. A preferred mole ratio of additional inhibitor to silver oxide in the silicone elastomer is about 1:40.

EXAMPLES

Example 1

Present 50 grams silicone part A; then
Add 50 grams of silicone part B to part A; then
Add 0.08 ml of inhibitor to the part A/part B mixture to provide a silicone elastomer; then
Disperse additional inhibitor throughout the part A/part B silicone elastomer; then
Add 7.5 grams silver oxide to the inhibitor/silicone elastomer mixture; then
Disperse silver oxide throughout the inhibitor/silicone elastomer mixture.

The work-time of the antimicrobial silicone elastomer thus formed is on the order of several hours to two days Example 2

Present 50 grams of silicone part B; then
Add 0.12 ml of additional inhibitor to silicone part B; then
Disperse the additional inhibitor throughout part B; then
Add 11.1 grams silver oxide to the inhibitor/part B mixture; then
Disperse the silver oxide throughout inhibitor/part B mixture; then
Add 50 grams silicone part A to inhibitor/silver oxide/part B mixture; then
Disperse silicone part A throughout previous mixture.

Elastomers made in accordance with either Example 1 or Example 2 provide a viscous, injection-moldable antimicrobial composition having a work-time of several hours to two days. For example, an addition cure silicone such as those known as gum-stock silicones could be used in lieu of an injection moldable silicone elastomer, maintaining generally the same chemical makeup and curing mechanism, but providing a different presentation for working with and molding the material. While particular embodiments of the present invention have been illustrated and described, it would be obvious to those skilled in the art that various other changes and modifications can be made without departing from the spirit and scope of the invention. For example, a further method for making an antimicrobial elastomeric composition may comprise the steps of: (a) presenting Part A and Part B of a silicone elastomer wherein when Part A and Part B are mixed together in the presence of an initiator, a curable, injection moldable silicone elastomer is formed; (b) adding additional inhibitor to Part A or Part B; (c) dispersing particles of an antimicrobial agent in Part A and Part B; and (d) mixing Part A with Part B. It is therefore intended to cover in the appended claims all such changes and modifications that are within the scope of this invention.

What I claim is:

1. A method for making an antimicrobial elastomeric composition comprising the steps of:
   (a) presenting Part A and Part B of a silicone elastomer wherein at least one of Part A and Part B includes a first amount of a first inhibitor, and wherein when Part A and Part B are mixed together, a curable silicone elastomer is formed;
   (b) mixing part A, part B, a second amount of a second inhibitor that increases a cure time of the curable silicone elastomer, and an antimicrobial work-time altering agent comprising silver oxide to form a curable silicone elastomer dispersion, said second amount is about 0.05 to about 0.40 weight % of said dispersion and relates to an amount of said antimicrobial work-time altering agent present in said dispersion.

2. The method for making an antimicrobial elastomeric composition in accordance with claim 1 wherein the inhibitor of said second amount of inhibitor is 2-methyl-3-butyn-2-ol.

3. A method for making an antimicrobial elastomeric composition comprising the steps of:
   (a) presenting Part A and Part B of a curable silicone elastomer wherein at least one of Part A and Part B includes a first amount of an inhibitor, and wherein when Part A and Part B are mixed together, the curable silicone elastomer is formed;
   (b) adding a second amount of an inhibitor to either Part A or Part B wherein the second inhibitor is any agent that increases the cure time of the curable silicone elastomer;
   (c) dispersing particles of an antimicrobial work-time altering agent comprising silver oxide into at least one of Part A and Part B; and (d) mixing Part A with Part B, wherein the second amount of an inhibitor added to either Part A or Part B prior to said mixing is present at a mole ratio of about 1:40 of said second inhibitor to said antimicrobial work-altering agent, wherein said second amount of inhibitor is effective to increase a work-time of the curable silicone elastomer comprising the antimicrobial work-altering agent prior to curing.

4. The method for making an antimicrobial elastomeric composition in accordance with claim 3 wherein the inhibitor of said second amount of an inhibitor is 2-methyl-3-butyn-2-ol.

5. The method for making an antimicrobial elastomeric composition in accordance with claim 1 wherein said antimicrobial work-time altering agent is 5-50% w/w silver oxide and the inhibitor of said second amount of an inhibitor is 2-methyl-3-butyn-2-ol and wherein the mole ratio of said second amount of an inhibitor to silver oxide in the curable silicone elastomer is about 1:40.

6. The method for making an antimicrobial elastomeric composition in accordance with claim 3 wherein said antimicrobial work-time altering agent is 5-50% w/w silver oxide and the inhibitor of said second amount of an inhibitor is 2-methyl-3-butyn-2-ol and wherein the mole ratio of said second amount of an inhibitor to silver oxide when Part A and Part B are mixed is about 1:40.

7. A method for making an antimicrobial elastomer composition in accordance with claim 1 wherein said curable silicone elastomer is an addition cure silicone elastomer.

8. A method for making an antimicrobial elastomer composition in accordance with claim 3 wherein said curable silicone elastomer is an addition cure silicone elastomer.

9. The method according to claim 1, wherein said mixing further comprises combining said Part A with said Part B, then adding said second amount of said second inhibitor, followed by adding said antimicrobial work-time altering agent.

10. The method according to claim 1, wherein said mixing further comprises first adding said second amount of said second inhibitor into either of said Part A or said Part B prior to combining said Part A with said Part B.

11. The method according to claim 10, wherein said mixing further comprises adding said antimicrobial work-time altering agent into either of said Part A or said Part B, and then combining said Part A with said Part B.

12. The method according to claim 10, wherein said mixing further comprises adding said antimicrobial work-time altering agent into both said Part A and said Part B, and then combining said Part A with said Part B.

13. The method according to claim 1, wherein said mixing further comprises adding said second amount of said second inhibitor to both said Part A and said Part B prior to adding said antimicrobial work-time altering agent to either of said Part A or said Part B, prior to combining said Part A with said Part B.

14. A method for injection molding an antimicrobial elastomeric composition, the method comprising:
 presenting Part A and Part B of a curable silicone elastomer wherein at least one of Part A and Part B includes a first amount of a first inhibitor;
 mixing said Part A, said Part B, a second amount of a second inhibitor, and an antimicrobial work-time altering agent comprising silver oxide, to form a curable and flowable silicone elastomer dispersion for injection molding, wherein said second amount of said second inhibitor is related to an amount of said antimicrobial work-time altering agent present in said dispersion and is effective to increase a work-time for injecting said dispersion, wherein in the absence of said second amount of inhibitor, a comparative mixture of said Part A, said Part B, and said antimicrobial work-time altering agent comprising silver oxide has a comparative work-time that is less than said work-time;
 injecting said dispersion into a mold, wherein said dispersion conforms to a contour of said mold during said injecting; and
 curing said curable silicone elastomer dispersion to form the antimicrobial elastomeric composition.

15. The method according to claim 14, wherein a mole ratio of said second amount of said second inhibitor to said amount of antimicrobial work-time altering agent in said dispersion is about 1:40.

16. The method according to claim 14, wherein said second amount of said inhibitor in said dispersion is about 0.05 to about 0.40 weight % of said total dispersion.

* * * * *